United States Patent
Fields et al.

(10) Patent No.: US 11,400,071 B2
(45) Date of Patent: *Aug. 2, 2022

(54) HEST G-18-0 AND BENZOYL PEROXIDE COMPOSITIONS AND METHODS FOR USING THE SAME

(71) Applicant: RODAN & FIELDS, LLC, San Francisco, CA (US)

(72) Inventors: Kathy Ann Fields, San Francisco, CA (US); Kathryn Pregerson Rodan, Oakland, CA (US); George Paul Majewski, Walnut, CA (US); Timothy John Falla, Woodinville, WA (US); Dzung Q. Le, Salt Lake City, UT (US)

(73) Assignee: Rodan & Fields, LLC, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/909,128

(22) Filed: Jun. 23, 2020

(65) Prior Publication Data

US 2020/0338037 A1 Oct. 29, 2020

Related U.S. Application Data

(63) Continuation of application No. 15/616,601, filed on Jun. 7, 2017, now Pat. No. 10,722,488.

(60) Provisional application No. 62/346,911, filed on Jun. 7, 2016.

(51) Int. Cl.
| | | |
|---|---|---|
| *A61K 31/327* | (2006.01) | |
| *A61K 31/19* | (2006.01) | |
| *A61K 9/00* | (2006.01) | |
| *A61K 9/06* | (2006.01) | |
| *A61K 47/10* | (2017.01) | |
| *A61K 31/08* | (2006.01) | |
| *A61K 9/08* | (2006.01) | |
| *A61K 47/12* | (2006.01) | |
| *A61J 1/20* | (2006.01) | |

(52) U.S. Cl.
CPC .......... *A61K 31/327* (2013.01); *A61K 9/0014* (2013.01); *A61K 9/08* (2013.01); *A61K 31/08* (2013.01); *A61K 31/19* (2013.01); *A61K 47/10* (2013.01); *A61K 47/12* (2013.01); *A61J 1/2093* (2013.01)

(58) Field of Classification Search
CPC ........ A61K 31/327; A61K 31/19; A61K 9/00; A61K 9/06; A61K 47/10
See application file for complete search history.

(56) References Cited

U.S. PATENT DOCUMENTS

| | | |
|---|---|---|
| 5,545,407 A | 8/1996 | Hall et al. |
| 2003/0068287 A1 | 4/2003 | Ansara et al. |
| 2007/0207104 A1 | 9/2007 | Borish |
| 2010/0029762 A1 | 2/2010 | Graeber et al. |
| 2017/0348274 A1 | 12/2017 | Fields et al. |

OTHER PUBLICATIONS

Gennaro "Remington: The Pharmaceutical Sciences, 18th Ed." 1995, Mack Publishing Co., Easton, PA (Cover and TOC only).
Santus et al. "Transdermal Enhancer Patent Literature" May 27, 1993, J. Controlled Releases 25(1-2):1-20.
Skrovankova et al. "Bioactive Compounds and Antioxidant Activity in Different Types of Berries" Oct. 2015, Int. J. Mol. Sci. 16(10):24673-24706.
Sun et al. "Improving the Solubility of Benzoyl Peroxide: A Review" Jul. 1, 2011, Cosmetics & Toiletries pp. 1-5.

*Primary Examiner* — Samira J Jean-Louis
(74) *Attorney, Agent, or Firm* — Troutman Pepper Hamilton Sanders LLP

(57) ABSTRACT

The compositions of the various embodiments include benzoyl peroxide and Hest G-18-0. The methods of this invention include treating acne, increasing the solubility of benzoyl peroxide, and treating the skin. Embodiments are also directed to a dual chamber package comprising a chamber for benzoyl peroxide and a chamber for Hest G-18-0.

27 Claims, 4 Drawing Sheets

HEST G-18-0 AND BENZOYL PEROXIDE COMPOSITIONS AND METHODS FOR USING THE SAME

CROSS-REFERENCE TO RELATED APPLICATIONS

This application is a continuation application of U.S. patent application Ser. No. 15/616,601 filed Jun. 7, 2017, which claims the benefit of U.S. Provisional Application No. 62/346,911, filed Jun. 7, 2016, which are incorporated by reference in their entirety.

SUMMARY

In some embodiments, a topical composition comprising an effective amount of benzoyl peroxide and an effective amount of Hest G-18-0 is disclosed. In some embodiments, a method of treating acne comprising applying to the skin of a subject an effective amount of benzoyl peroxide and an effective amount of Hest G-18-0 is provided. In some embodiments, a method of improving the solubility of benzoyl peroxide in a topical composition comprising applying to the skin of a subject an effective amount of benzoyl peroxide and an effective amount of Hest G-18-0 is provided. In some embodiments, a method of treating the skin of a subject comprising applying to the skin of a subject an effective amount of benzoyl peroxide and an effective amount of Hest G-18-0 is disclosed. In some embodiments, a dual chamber package comprising a chamber containing benzoyl peroxide and a chamber containing Hest G-18-0 is provided.

DETAILED DESCRIPTION

Figure 1:
FIG. 1 illustrates the solubility of benzoyl peroxide in Hest G-18-0 or ethoxydiglycol.

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

As used herein and in the appended claims, the singular forms "a," "an," and "the" include plural reference unless the context clearly dictates otherwise. Thus, for example, reference to a "cell" is a reference to one or more cells and equivalents thereof known to those skilled in the art.

As used herein, the term "about" means plus or minus 10% of the numerical value of the number with which it is being used. Therefore, about 100 mg means in the range of 90 mg-110 mg.

"Administering" when used in conjunction with a composition means to administer a composition to a patient whereby it positively impacts the tissue to which it is targeted, e.g. the skin. "Administering" a composition may be accomplished by, for example, topical administration, or in combination with other known techniques. Administering may be self-administration, wherein the subject in need of such treatment administers a composition or administering may be by a medical or other health care professional or a caretaker of the subject in need of such treatment.

The term "animal," "patient," or "subject" as used herein includes, but is not limited to, humans and non-human vertebrates such as wild, domestic and farm animals.

As used herein, the terms "comprising," "comprise," "comprises," and "comprised" are inclusive or open-ended and do not exclude additional, unrecited elements or method steps.

As used herein, the term "consists of" or "consisting of" means that the composition or method includes only the elements, steps, or ingredients specifically recited in the particular embodiment or claim.

As used herein, the term "consisting essentially of" or "consists essentially of" means that the composition or method includes only the specified materials or steps and those that do not materially affect the basic and novel characteristics of the claimed invention.

The term "effective amount" refers to an amount of a composition, of the embodiments described herein, necessary or sufficient to achieve the desired effect. For example, in some embodiments, the desired effect may include, without limitation, medically therapeutic, cosmetically therapeutic and/or prophylactic treatment, as appropriate; increasing the solubility of benzoyl peroxide; decreasing the surface tension of the composition; increasing the wettability of the surface of the skin or skin lesion; increasing the permeability of the composition into the subject's skin, skin lesion, or surface imperfections, including crevices, invaginations and irregularities of the skin or skin lesion (e.g. acne, a pimple, a comedo, a breakout); decreasing the size of the target lesion; improving the shape and/or appearance of the target lesion; improving the target lesion or treated area and/or removing the target lesion; treating acne; reducing or eliminating erythema or redness of the skin; reducing or eliminating irritation of the skin; decreasing or eliminating any drying of the skin; decreasing or eliminating cracking of the skin; and decreasing or eliminating the appearance of white residue on the skin; or a combination thereof. The specific dose and effective amount of a compound administered according to embodiments of the present invention to obtain therapeutic and/or prophylactic effects will, of course, be determined by the particular circumstances surrounding the case, including, for example, the sensitivity of the subject's skin, and the severity of the condition being treated, and therefore, the dosage ranges are not intended to limit the scope of the invention in any way.

As used herein, the term "pharmaceutically acceptable" and grammatical variations thereof, as they refer to carriers, diluents, excipients, and reagents or other ingredients of the composition, represent that the materials used in the final composition are not irritating or otherwise harmful to the patient in general and to the skin, in particular, and preferably are pleasant and well tolerated with respect to general appearance, pH, color, smell and texture (feel), that they are not, for example, unacceptably sticky (tacky), oily or drying, and that they do spread easily, absorb into the skin at an acceptable rate of absorption, and are generally moisturizing.

The term "skin" as used herein refers to the organ of the body which protects the subject from environmental irritations, regulates the body's temperature and allows for external sensations. The "skin" is separated into three layers: the outermost layer called the epidermis which contains melanocytes; the dermis which contains connective tissue, hair follicles and sweat glands; and the deepest subcutaneous layer called the hypodermis which is made up of fat and connective tissue.

"Topical application" or "topical administration" refers to the delivery of a composition, for treating conditions of the epidermis. Topical administration of a drug may often be advantageously applied in, for example, the treatment of various skin disorders.

"Topical compositions," as described herein, are compositions that are applied to skin. "Topical compositions" may, for example, be used to confer therapeutic benefit to a patient or cosmetic benefits to a consumer. "Topical compositions" are advantageous in that it avoids first-pass metabolism, circumvents gastrointestinal absorption, can allow delivery of an active ingredient with a relatively short biological half-life and/or a narrow therapeutic window, and can allow delivery of an active ingredient to a localized spot on the skin.

The terms "treat," "treated," or "treating" as used herein refers to therapeutic treatment, cosmetic treatment and/or prophylactic or preventative measures, wherein the object is to prevent, reduce, eliminate or slow down (lessen) an undesired physiological condition, disorder or disease, or to obtain beneficial or desired clinical results (e.g. decrease acne, comedones, pimples, or breakouts). For the purposes of this disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of unwanted side effects.

Acne vulgaris ("acne") is a disorder resulting from the action of hormones on the skin's oil glands (sebaceous glands), wherein the sebaceous glands of the skin produce excess sebum, and become enlarged and/or infected when the pore opening becomes plugged with a comedo (a mixture of keratin and sebum). The symptoms of acne include plugged pores and outbreaks of inflamed lesions commonly called pimples.

Acne lesions usually occur on the face, neck, back, chest, and shoulders. It is the most common skin disease amongst teenagers and young adults. Acne can occur at any age, and is common to all ethnic backgrounds. Nearly 85 percent of people between the ages of 12 and 24 develop this disorder. For most people, acne tends to go away by the time they reach their thirties. However, some people in their forties and fifties continue to have acne, commonly termed "adult acne."

Several acne treatments are commercially available, such as those in the following categories, for example: topical bactericidals (e.g. triclosan, chlorhexidine gluconate and benzoyl peroxide); topical antibiotics (e.g. erythromycin, tetracycline and clindamycin); oral antibiotics (e.g. tetracyclines and trimethoprim); hormonal treatments (e.g. hormonal contraception in females); topical retinoids (e.g. tretinoin, adapalene and tazarotene); oral retinoids (e.g. isotretinoin, marketed as Accutane®, Roche Pharmaceuticals, New Jersey); and phototherapy.

Many of the over-the-counter ("OTC") acne medications currently marketed rely on chemicals which have an antibacterial and/or a peeling/drying action which aids in breaking down keratin (i.e. keratolytic agent), thus helping to clear plugged pores.

Consequently, there are a wide variety of drugs that are used in topical compositions for the treatment of acne, and there are disadvantages in respect of each drug or combination of drugs. Benzoyl peroxide, resorcinol, salicylic acid, and sulfur are among the most common topical OTC agents used to treat acne. Specifically, benzoyl peroxide is effective as an antibacterial by producing an unwelcome environment for the survival of the bacteria, *Propionibacterium acnes*, known to cause acne; it acts as a peeling agent by increasing cell turnover and helping to clear plugged pores, additionally, it decreases inflammatory lesions.

In general, topical formulations used to treat acne must be water-based, as oil-based formulations can cause or further aggravate acne eruptions.

Benzoyl peroxide is a crystalline solid with a melting point of 103° C. to 106° C., and is insoluble in water. Benzoyl peroxide has the molecular formula $[C_6H_5C(O)]_2 O_2$ and the structure as provided below (Formula I):

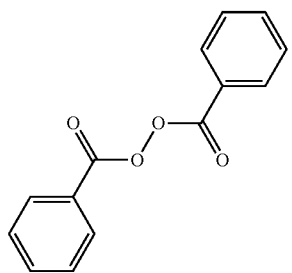

Benzoyl peroxide is practically insoluble in common cosmetic solvents, such as ethanol, glycerin, propylene glycol, or butylene glycol. Benzoyl peroxide is soluble in organic solvents, however, most organic solvents are toxic and therefore not suitable for pharmaceutical and cosmetic use. Polar organic solvents such as acetone and ethanol are less toxic, but the flammability of these solvents as well as the ability of these solvents to irritate and strip the skin of its protective mantle limit their use in pharmaceutical and cosmetic compositions. The solubility of benzoyl peroxide in water is only 9.1 ppm at 25° C., therefore, most acne products provide benzoyl peroxide as a suspension of a fine powder consisting of various sized clumps of benzoyl peroxide molecules. These particulate dispersions of benzoyl peroxide often build agglomerates over time in formulations to further reduce the effective surface area of the dispersed benzoyl peroxide particles. When applied to the skin, this suspension has limited penetration and, therefore, limited efficacy, consequently requiring high concentrations of benzoyl peroxide to be effective. As a result, of the high concentration of benzoyl peroxide, which are generally insoluble, the subject often experiences erythema, irritation, drying, and cracking of the skin, and the appearance of white residue (undissolved, crystalline benzoyl peroxide) on the skin. Furthermore, it is difficult for the benzoyl peroxide crystals to penetrate into the comedo and into the sebaceous gland itself, because the comedo plug is a physical barrier and the size of the follicular opening is limited.

Consequently, commercially available topical formulations of benzoyl peroxide have several disadvantages, since they: (1) have a limited ability to penetrate the skin and consequently have low efficacy for the dose administered; (2) cannot be formulated as clear compositions and sprays; (3) causes erythema and irritation to the skin; (4) causes dryness and cracking of the skin; and (5) leaves an aesthetically undesirable white, powder residue on the skin once the topical formulation dries.

Further, such disadvantages and adverse effects translate into poor user compliance of benzoyl peroxide products. As a result of poor compliance, users experience decreased efficacy, e.g. no improvement in the condition of acne, or a long delay in any noticeable improvement of acne. By improving the delivery and solubility of benzoyl peroxide, the adverse effects of dryness, cracking of the skin, erythema, irritation, and appearance of unattractive white residue on skin are eliminated, which translates into better patient compliance and, in turn, improved efficacy and tolerability of benzoyl peroxide products.

It has taken decades for the industry to realize that improving the solubility of benzoyl peroxide could improve efficacy and decrease irritation. It had been the widespread belief that benzoyl peroxide is a strong oxidizing agent, and solubilizing it would be more reactive than its crystalline powder, as such, erythema, irritation and dryness would increase. Before the embodiments of the present invention, the only solvents used to dissolve benzoyl peroxide were benzyl benzoate and dimethyl isosorbide, each having a similar structure to benzoyl peroxide. This lead the industry to believe that the solubility of benzoyl peroxide required solvents with a very specific molecular structure, one similar to benzoyl peroxide, to produce a solution, not a suspension. Accordingly, the industry continues to test solvents based upon this "like dissolves like" rule. See *Sun and Sun, Improving the Solubility of Benzoyl Peroxide: A Review, Cosmetics & Toiletries* (Jul. 1, 2011). As a result, very little progress has been made.

Embodiments of the present invention has unexpectedly solved this solubility problem. The surprising solvent for benzoyl peroxide is glycereth-18-ethylhexanoate, a high molecular weight polymer. Glycereth-18-ethylhexanoate increasing the solubility of benzoyl peroxide, thus increasing the efficacy of benzoyl peroxide and decreasing or eliminating unwanted side effects. This increase in solubility improves benzoyl peroxide delivery, increases anti-microbial efficacy and reduces erythema, irritation, drying, and cracking of the skin and produces a transparent composition which does not leave a white residue on the skin.

As described in U.S. Patent Publication No. 2007/0207104, which is incorporated here by reference, glycereth-18 ethylhexanoate has the molecular formula: $C_{47}H_{94}O_{22}$ with a molecular weight of 1010 grams per mole. Glycereth-18 ethylhexanoate is the ester of ethylhexanoic acid with a polyethylene glycol ether of glycerin containing an average of 18 moles of ethylene oxide and conforms generally to the formula shown below (Formula II):

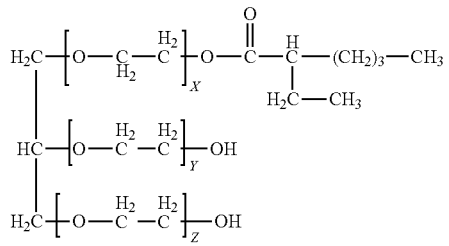

where x+y+z have an average value of 18. Glycereth-18-ethylhexanoate is assigned CAS No. 827307-65-6, and is known to include glycereth-18-hexanoate and glycereth-18; for purposes of this specification, this composition will be referred to as "Hest G-18-0." Hest G-18-0 has a typical International Nomenclature of Cosmetic Ingredients (INCI) composition of glycereth-18 (25-50%) and glycereth-18 ethylhexanoate (>50%).

Hest G-18-0 is non-irritating, soluble in water and alcohol. Its heat of solution is exothermic delivering a warming effect 2-3 times that of glycerin when applied to the skin. Hest G-18-0 is an effective anti-microbial agent with activity against a wide range of microorganisms.

Compositions

In certain embodiments, a topical composition comprises an effective amount of benzoyl peroxide and an effective amount of Hest G-18-0. In certain embodiments, a topical composition consists of an effective amount of benzoyl peroxide and an effective amount of Hest G-18-0. In certain embodiments, a topical composition consists essentially of an effective amount of benzoyl peroxide and an effective amount of Hest G-18-0. In some embodiments, the topical composition is a solution of benzoyl peroxide.

In embodiments described herein, the topical composition comprises both an effective amount of Hest G-18-0 and an effective amount of benzoyl peroxide in a single composition. In embodiments described herein, the topical composition consists of both an effective amount of Hest G-18-0 and an effective amount of benzoyl peroxide in a single composition. In embodiments described herein, the topical composition consists essentially of both an effective amount of Hest G-18-0 and an effective amount of benzoyl peroxide in a single composition.

In certain embodiments, the topical composition is applied directly to the skin as a single composition containing an effective amount of Hest G-18-0 and an effective amount of benzoyl peroxide.

In embodiments described herein, an effective amount of Hest G-18-0 and an effective amount of benzoyl peroxide are provided in two separate topical compositions. In certain embodiments, an effective amount of benzoyl peroxide is applied to the skin of the subject prior to, during, or after the application of an effective amount of Hest G-18-0.

In embodiments described herein, benzoyl peroxide is at a concentration from about 1% to about 10% by weight of the final composition. In embodiments described herein, benzoyl peroxide is at a concentration of about 1%, about 2.5%, about 5%, about 10%, or greater than 10% by weight of the final composition. In embodiments described herein, benzoyl peroxide is at a concentration of about 10% by weight of the final composition. In embodiments described herein, benzoyl peroxide is at a concentration of about 2.5% by weight of the final composition.

In embodiments described herein, Hest G-18-0 is at a concentration ranging from about 0.1% to about 90% by weight of the final composition. In embodiments described herein, the Hest G-18-0 is at a concentration ranging from about 0.5% to about 65% by weight of the final composition. In embodiments described herein, the Hest G-18-0 is at a concentration ranging from about 5% to about 40% by weight of the final composition. In embodiments described herein, the Hest G-18-0 is at a concentration ranging from about 5% to about 20% by weight of the final composition. In embodiments described herein, the Hest G-18-0 is at a concentration ranging from about 1% to about 15%, about 10% to about 65%, or about 20% to about 45% by weight of the final composition.

The pH of a topical composition, as described herein, is between 3 and 10. For pH adjustment, any agent commonly used in the laboratory for pH adjustment, such as hydrochloric acid or sodium hydroxide, can be used. Other acids such as acetic acid, benzoic acid, formic acid, fumaric acid, lactic acid, phosphoric acid, sulfuric acid or other organic and/or inorganic acids, as known to those skilled in the art, could also be used. Other bases such as ammonium hydroxide, ethanolamine, magnesium hydroxide, sodium or potassium bicarbonate, sodium or potassium hydroxide, organic and/or inorganic bases, as known to those skilled in the art, could also be used.

In embodiments described herein, viscosifiers are added to the topical compositions to increase the viscosity to enable it to adhere to a surface, or to improve how the composition feels to one's touch when it is being used or applied. In embodiments described herein, a thickening agent is added to the topical composition to stabilize the dispersion until use. In embodiments described herein, viscosifiers utilized include carageenans; cellulose compounds such as methyl cellulose, hydroxymethyl cellulose, acrylamide/sodium acryloyldimethyl taurate copolymer and carboxymethyl cellulose; pectin; dextrans of various molecular weight ranges; starch; gum tragacanth; gum arabic; guar gum; acacia gum; gum karaya; silica, diatomaceous earth; and other commonly used agents known to those skilled in the art. In embodiments described herein, the general range for the addition of a viscosifier is in the range from about 0.001% to about 10%.

In embodiments described herein, the topical compositions of the present invention may also be formulated to include other chemical penetration enhancers which have significant ability to enhance transport of actives. Such substances may have the character of surfactants, a zone-like compounds, solvents, alcohols, fatty acids, fatty esters, aliphatic thiols and the like. Examples of chemical penetration enhancers are reported in the paper of Santus et al. (Santus, C. G. and Baker, R. W., Transdermal enhancer patent literature. Journal of Controlled Release 1993.25:1-20.)

In embodiments described herein, other ingredients such as, but not limited to, preservatives, colorants and fragrances are added to the topical composition.

In embodiments described herein, one or more preservatives are added to the composition. Examples of such preservatives are butylated hydroxyanisole ("BHA"), butylated hydroxytoluene ("BHT"), phenol, resorcinol; parabens such as methyl paraben, ethyl paraben, propyl paraben, butyl paraben, isopropyl paraben, isobutyl paraben, 2-phenoxyethanol, 1,3-Octandiol; sodium benzoate, benzyl alcohol, or other preservatives commonly used in the industry. Other phenolic agents include 4,6-di-tert-butyl-resorcinol, 2,6-di-tert-butylphenol, 2,5-di-tert-butylphenol, 3,5-di-tert-butylphenol, 2,6-di-tert-hexylphenol, 2,6-di-tert-octylphenol and 2,6-di-tert-decylphenol. The general range for addition of preservatives is from about 0.01% to about 10% by weight of the composition.

In embodiments described herein, one or more colorants are added to the topical composition. The colorant is added to the topical composition in a range from about 0.00001% to about 5%.

In embodiments described herein, fragrances are added to the composition. The fragrance is added to the composition in a range from about 0.001% to about 20%. Examples of fragrances that could be used include, for example only and are not intended to be limited, ammonium glycyrrhizate, amyl acetate, anisaldehyde, benzoic acid, betula alba extract, caraway fruit oil, safflower seed oil, caramel, cedarwood oil, cinnamyl acetate, citrus extracts such as from orange, grapefruit, lemon or lime, citronella, carrot, clove, eucalyptus, wintergreen, licorice, lavender, cherry, various berries or the like.

In embodiments described herein, the cosmetically acceptable excipient can be at least one ingredient selected from: polysaccharide polymer, glycerin, butylene glycol, dipropylene glycol, pentylene glycol, polyethylene glycol, ethanol, and water. In embodiments described herein, the cosmetically acceptable excipient may also include one or more cosmetically or pharmaceutically acceptable carriers. Suitable carriers that may be used in the topical compositions discussed herein are known in the art and include, but are not limited to, solubilizers such as C2 to C8 straight and branched chain alcohols, diols and triols, moisturizers and humectants such as glycerine, amino acids and amino acid derivatives, polyaminoacids and derivatives, pyrrolidone carboxylic acids and their salts and derivatives, surfactants such as sodium laureth sulfate, sorbitan monolaurate, emulsifiers such as cetyl alcohol, stearyl alcohol, thickeners such as methyl cellulose, ethyl cellulose, hydroxymethylcellulose, hydroxypropylcellulose, polyvinylpyrrolidone, polyvinyl alcohol and acrylic polymers. Other examples of suitable excipients, such as binders and fillers are listed in Remington's Pharmaceutical Sciences (18th Edition, Ed. Alfonso Gennaro, Mack Publishing Co. Easton, Pa., 1995) and Handbook of Pharmaceutical Excipients (3rd Edition, Ed. Arthur H. Kibbe, American Pharmaceutical Association, Washington, D.C. 2000).

In embodiments described herein, the topical compositions of the present invention may include a secondary skin care active. "Skin care active" means all compounds or substances that provide a benefit when applied to skin. Skin care actives may provide benefits, or claimed benefits, in areas such as one or more of wrinkle removal or wrinkle reduction, firming of skin, exfoliation of skin, skin lightening, treatment of dandruff, treatment of acne, skin conditioning, development of tans and artificial tans, improvement of skin moisture content, improvement of skin barrier properties, control of sweat, anti-aging, reduction or avoidance of irritation and reduction or avoidance of inflammation. Examples of skin care actives include molecules such as peptides, proteins, oligonucleotides, fullerenes as well as small molecules. Skin care actives may be protease and/or enzyme inhibitors, anti-coenzymes, chelating agents, antibodies, antimicrobials, humectants, vitamins, skin protectants, antioxidants and/or skin soothing agents, plant extracts and the like. Examples of skin care actives include but are not limited to vitamin C, vitamin E (alpha tocopherol), retinoids, soy derivatives (e.g. isoflavones), green tea polyphenols, alpha hydroxy acids (e.g. glycolic and lactic acids), beta hydroxy acids (e.g. salicylic acid), poly hydroxy acids, alpha lipoic acid, hemp oil (glycerides), niacinamide, dimethyl amino ethanol, coenzyme Q10, capryloyl glycine, undecylenoyl glycine, octenidine HCl, elubiol, 1,2 hexanediol, oligopeptide-10, bakuchiol, 4-Hydroxy-cyclohexanecarboxylic acid butyl ester, nigella sativa oil, cinnamon bark extract, quercetin, ECGC, blueberry extract, resveratrol and pterostilbene, betaglucan, kinetin (plant growth hormone), dimethyl sulfone and botulinum toxin. Other examples of skin care actives may be found in The Perricone Prescription (Nicholas Perricone, Harper Collins Publishers Inc., New York, 2002).

The topical compositions of the present invention may be formulated by those skilled in the art as liquids, toners, solutions, sprays, emulsions, moisturizers, sunscreens, creams, lotions, masks, suspensions, triturates, gels, jellies, pastes, foams, ointments, shampoos, adhesives, serums, treated clothes or pads and the like.

In embodiments described herein, the topical compositions may be applied to the skin by any means known in the art including, but not limited to, by an aerosol, spray, pump-pack, brush, swab, or other applicator. Preferably, the applicator provides either a fixed or variable metered dose application such as a metered dose aerosol, a stored-energy metered dose pump or a manual metered dose pump.

In certain embodiments, the topical formulation is a Hest irritation mitigation Emollient Gel for pre, post or dual chamber application with 2.5-10% BPO topical OTC, comprising 65% Hest G-18-0, 3% hydroxypropyl methylcellulose, 31.94% water, and 0.06% triethanolamine.

In certain embodiments, the topical formulation is a benzoyl peroxide Cream Gel, comprising 83.3% water, 8% glycerin, 1% Octenidine HCl/Ethylhexylglycerin, 2.5% benzoyl peroxide, 0.2% *Curcuma wenyujin/Curcuma kwangsiensis* Rhizome Extract, 3.5% Acrylamide/Sodium Acryloyldimethyl Taurate Copolymer, Isohexadecane, Polysorbate 80, 1% Dimethicone, Polysilicone-11, *Butyrospermum parkii* (Shea) Butter, and 0.5% methyl methacrylate crosspolymer.

In certain embodiments, the topical formulation is a benzoyl peroxide Cream Gel with Hest, comprising 53.3% water, 40% Glycereth-18 and Glycereth-18 Ethylhexanoate, Water, Hydroxypropyl Methylcellulose, TEA, 1% Octenidine HCl/Ethylhexylglycerin, 2.5% benzoyl peroxide, 0.2% *Curcuma wenyujin/Curcuma kwangsiensis* Rhizome Extract, 1.5% Acrylamide/Sodium Acryloyldimethyl Taurate Copolymer, Isohexadecane, Polysorbate 80, 1% Dimethicone, Polysilicone-11, *Butyrospermum parkii* (Shea) Butter, and 0.5% methyl methacrylate crosspolymer.

In certain embodiments, the topical formulation is a Hest irritation mitigation toner serum for pre, post or dual chamber application with 2.5-10% BPO topical OTC, comprising 12% Glycereth-18 Ethylhexanoate, 1.5% capryloyl glycine, 0.5% tromethamine, 1% Phenoxyethanol, Caprylyl Glycol, Ethylhexylglycerin, Hexylene Glycol, 1% Propylene glycol (and) Ethylhexylglycerin (and) Octenidine HCl, 2% Propanediol, *Vaccinium angustifolium* (Blueberry) Fruit Extract, 64% water, 10% alcohol, 3.76% glycerin, 4% butylene glycol, 0.16% cetyl hydroxyethylcellulose, and 0.08% sodium hyaluronate.

In certain embodiments, the topical formulation is a Hest irritation mitigation toner serum for pre, post or dual chamber application with 2.5-10% BPO topical OTC, comprising 0.5% salicylic acid, 12% Glycereth-18 Ethylhexanoate, 1% capryloyl glycine, 0.5% tromethamine, 1% Phenoxyethanol, Caprylyl Glycol, Ethylhexylglycerin, Hexylene Glycol, 1% Propylene glycol (and) Ethylhexylglycerin (and) Octenidine HCl, 2% Propanediol, *Vaccinium angustifolium* (Blueberry) Fruit Extract, 66% water, 10% alcohol, and 6% butylene glycol, glycerine, cetyl hydroxyethylcellulose, sodium hyaluronate.

In certain embodiments, the topical formulation is a Hest irritation mitigation toner serum for pre, post or dual chamber application with 2.5-10% BPO topical OTC, comprising 0.5% salicylic acid, 13% Glycereth-18 Ethylhexanoate, 0.7% capryloyl glycine, 0.5% tromethamine, 1% Phenoxyethanol, Caprylyl Glycol, Ethylhexylglycerin, Hexylene Glycol, 1% Propylene glycol (and) Ethylhexylglycerin (and) Octenidine HCl, 1.5% Propanediol, *Vaccinium angustifolium* (Blueberry) Fruit Extract, 64.8% water, 1% dimethyl isosorbide, 10% alcohol, and 6% butylene glycol, glycerine, cetyl hydroxyethylcellulose, sodium hyaluronate.

In certain embodiments, the topical formulation is a Hest irritation mitigation toner serum for pre, post or dual chamber application with 2.5-10% BPO topical OTC, comprising 0.5% salicylic acid, 12% Glycereth-18 Ethylhexanoate, 1% Phenoxyethanol, Caprylyl Glycol, Ethylhexylglycerin, Hexylene Glycol, 1% Propylene glycol (and) Ethylhexylglycerin (and) Octenidine HCl, 1.5% Propanediol, *Vaccinium angustifolium* (Blueberry) Fruit Extract, 63% water, 10% alcohol, and 6% butylene glycol, glycerine, cetyl hydroxyethylcellulose, sodium hyaluronate.

In certain embodiments, the topical formulation is a Hest irritation mitigation wipe for pre-application with 2.5-10% BPO topical OTC, comprising 40% Hest-G-18-0, 35% alcohol, 23.4% water, 0.1% bisabolol, 1% Ethylhexylglycerin, Octenidine HCl, and 0.5% polysorbate 20.

In certain embodiments, the topical formulation is a Hest irritation mitigation gel for pre, post or dual chamber application with 2.5-10% BPO topical OTC, comprising 64% Hest-G-18-0, 35.3% water, 0.5% carbomer, and 0.2% glucamine.

In certain embodiments, the topical formulation is a Hest irritation mitigation anhydrous gel for pre, post or dual chamber application with 2.5-10% BPO topical OTC, comprising 65% Hest-G-18-0, and 35% water.

In certain embodiments, the topical formulation is a Hest irritation mitigation lotion for pre, post or dual chamber application with 2.5-10% BPO topical OTC, comprising 15% Hest-G-18-0, 3.5% Acrylamide/Sodium Acryloyldimethyl Taurate Copolymer, Isohexadecane, Polysorbate 80, 70.5% water, 1% Octenidine HCl, Ethylhexylglycerin, 2% Ethylhexyl Palmitate, 5% Dimethicone, Polysilicone-11, *Butyrospermum parkii* (Shea) Butter, and 3% Caprylic/Capric Triglyceride.

In certain embodiments, the topical formulation is a Hest spot treatment adhesive acne dots for pre-application with 1.0-10% BPO topical, comprising 37.5% Hest-G-18-0, 1% PVP, 1% Vinyl Caprolactam/VP/Dimethylaminoethyl Methacrylate Copolymer, 35% alcohol, 0.1% bisabolol, 0.5% silica, 1% Ethylhexylglycerin, Octenidine HCl, and 0.5% polysorbate 20.

Methods of Use

In certain embodiments, a method of treating acne comprises applying to the skin of a subject an effective amount of Hest G-18-0 and an effective amount of benzoyl peroxide. In certain embodiments, a method of treating acne consists of applying to the skin of a subject an effective amount of Hest G-18-0 and an effective amount of benzoyl peroxide. In certain embodiments, a method of treating acne consists essentially of applying to the skin of a subject an effective amount of Hest G-18-0 and an effective amount of benzoyl peroxide.

In embodiments described herein, the efficacy of benzoyl peroxide is increased. The increased solubility of benzoyl peroxide provides for greater penetration into the comedo and into the sebaceous gland itself, resulting in a reduction or elimination of the symptoms of acne including plugged pores, and outbreaks of inflamed lesions or pimples.

In embodiments described herein, the unwanted side effects of erythema, irritation, drying, cracking of the skin, and appearance of white residue on the skin experienced with prior compositions of benzoyl peroxide are reduced or eliminated. In embodiments described herein, subject compliance is increased.

In certain embodiments, a method of improving the solubility of benzoyl peroxide in a topical composition comprises applying to the skin of a subject an effective amount of Hest G-18-0 and an effective amount of benzoyl peroxide. In certain embodiments, a method of improving the solubility of benzoyl peroxide in a topical composition consists of applying to the skin of a subject an effective amount of Hest G-18-0 and an effective amount of benzoyl peroxide. In certain embodiments, a method of improving the solubility of benzoyl peroxide in a topical composition consists essentially of applying to the skin of a subject an effective amount of Hest G-18-0 and an effective amount of benzoyl peroxide.

In embodiments described herein, the solubility of benzoyl peroxide is increased. The composition of benzoyl peroxide and Hest G-18-0 is transparent. Solubility is measured by visualizing whether the solid crystalline form of benzoyl peroxide disappears in the liquid or if it can be seen at the bottom of the solution in an undissolved crystalline form. See FIG. 1.

In certain embodiments, a method of treating the skin of a subject comprises applying to the skin of a subject an effective amount of Hest G-18-0 and an effective amount of benzoyl peroxide. In certain embodiments, a method of treating the skin of a subject consists of applying to the skin of a subject an effective amount of Hest G-18-0 and an effective amount of benzoyl peroxide. In certain embodiments, a method of treating the skin of a subject consists essentially of applying to the skin of a subject an effective amount of Hest G-18-0 and an effective amount of benzoyl peroxide.

In embodiments described herein, the unwanted side effects of erythema, irritation, drying, cracking of the skin, and appearance of white residue on the skin experienced with prior compositions of benzoyl peroxide are reduced or eliminated. In embodiments described herein, subject compliance is increased.

Dual Chamber Package

In certain embodiments, a dual chamber package comprises a chamber containing benzoyl peroxide and a chamber containing Hest G-18-0. In certain embodiments, a dual chamber package consists of a chamber containing benzoyl peroxide and a chamber containing Hest G-18-0. In certain embodiments, a dual chamber package consists essentially of a chamber containing benzoyl peroxide and a chamber containing Hest G-18-0.

Embodiments of the invention will be described with reference to the following Examples which are provided for illustrative purposes only and should not be used to limit the scope of or construe the invention.

EXAMPLES

Example 1: Solubility of Benzoyl Peroxide

In FIG. 1, beaker on the right, demonstrates that 5% benzoyl peroxide is completely dissolved in 100% Hest G-18-0, no crystals are apparent within the solution (a few air bubbles can be seen due to mixing). Compare this with FIG. 1, beaker on the left, where 5% benzoyl peroxide in 100% ethoxydiglycol, can be seen as white particles at the bottom of the beaker, demonstrating the insolubility of benzoyl peroxide in ethoxydiglycol.

Example 2: Decrease in Side Effects Associated with Benzoyl Peroxide Treatment

To test the hypothesis that an increase in benzoyl peroxide solubility would increase peroxide reactivity and thus increase its anti-microbial efficacy and reduced localized irritation, a commercially available 10% benzoyl peroxide product (Clean & Clear persa-gel 10) was applied to the skin of the left forearm of a subject directly or Hest G-18-0 was applied to the right forearm of a subject prior to the application of the 10% benzoyl peroxide product.

Figure 2A:
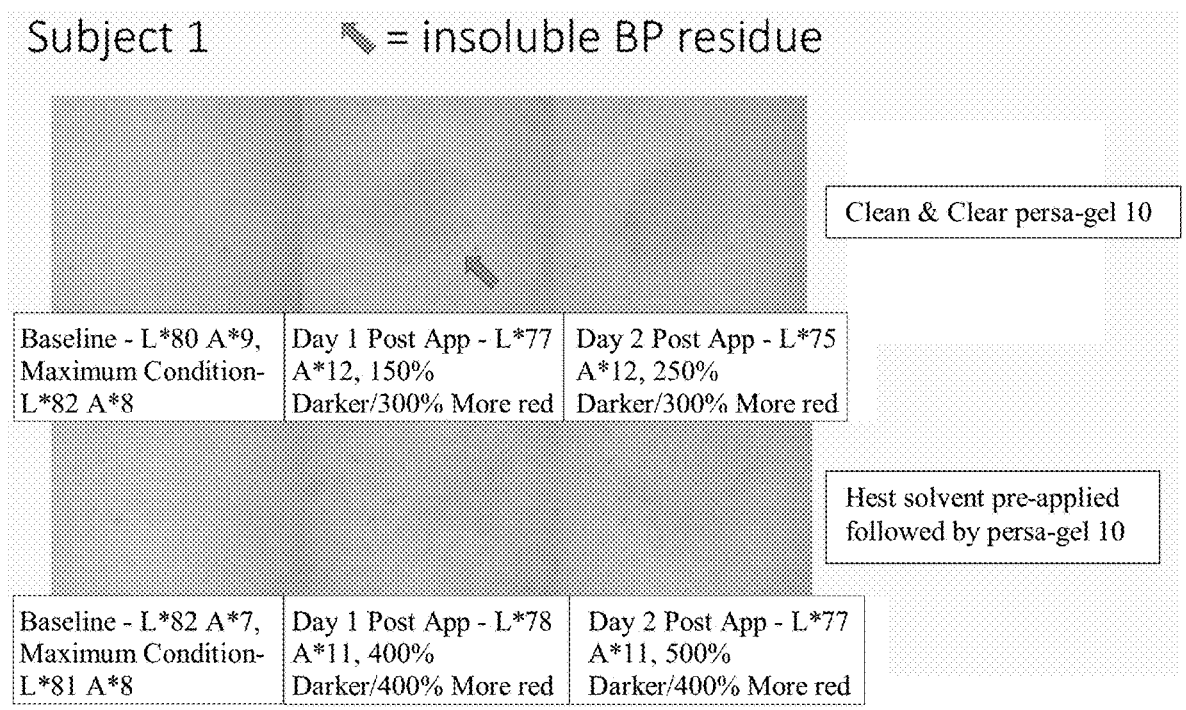
FIG. 2A and FIG. 2B illustrate the reduction of erythema of the skin and white residue on the skin in 2 subjects, where Hest G-18-0 was applied to the skin prior to application of benzoyl peroxide.
Figure 2B:
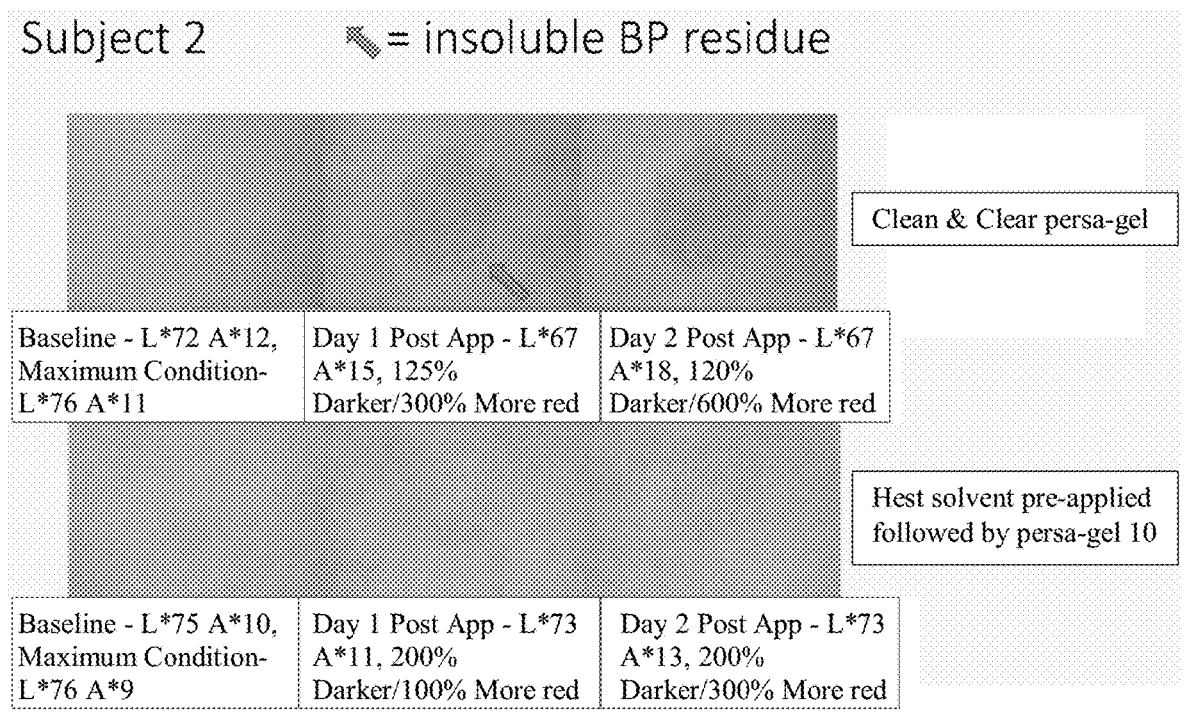

The results clearly demonstrate that the pre-application of Hest G-18-0 to the skin of the subject greatly reduced the erythema; compare the top panels (10% benzoyl peroxide only) of FIGS. 2A (subject 1) and 2B (subject 2) with the bottom panels (Hest g-18-0 and 10% benzoyl peroxide) of FIGS. 2A and 2B. This decrease in erythema can be seen 2 days post application. Additionally, no benzoyl peroxide white residue can be seen on the skin of the subject when Hest G-18-0 was pre-applied; compare day 1 post application in FIGS. 2A and 2B, insoluble benzoyl peroxide residue is identified by an arrow in the picture.

Example 3: Skin Irritation Study

A blind 24 hour patch test was performed. Consumer products or raw materials designed for consistent reapplication to areas of the skin may, under proper conditions, prove to be contact irritants in certain individuals. It is the intention of a 24 Hour Patch Test to provide a basis for evaluation of this irritation potential if such exists.

The test material was assigned a unique laboratory code number and entered into a daily log identifying the lot number, sample description, sponsor, date received and tests requested. The test samples were a commercial acne product containing 10% benzoyl peroxide (Code No. 0-5276) and a cosmetic emollient gel RF1507-25 2-12-16 (Code No. 0-5277, 65% Hest G-18-0).

Prior to induction of a human test panel, USP or CTFA Preservative Efficacy Test or equivalent and 90 Day Accelerated Stability and Container Compatibility Studies were conducted with no adverse results.

The panel selection included the following criteria: 1) Standards for Inclusion in the Study: individuals who are not currently under a doctor's care, individuals free of any dermatological or systemic disorder which would interfere with the results, individuals free of any acute or chronic disease that might interfere with or increase the risk of study participation, Individuals who will complete a preliminary medical history form and are in general good health, individuals who will read, understand and sign an informed consent document relating to the specific type of study they are subscribing. 2) Standards for Exclusion from the Study: individuals under 18 years of age, individuals who are currently under a doctor's care, individuals who are currently taking any medication (topical or systemic) that may mask or interfere with the test results, subjects with a history of any acute or chronic disease that might interfere with or increase the risk associated with study participation, individuals diagnosed with chronic skin allergies, female volunteers who indicate that they are pregnant or lactating, individuals with skin that is sunburned, irritated, sensitive or has recently been professionally exfoliated, resurfaced or waxed in the test site. Recruitment to the panel was accomplished by advertisements in local periodicals, community bulletin boards, phone solicitation, electronic media or any combination thereof.

The panel demographics, which included 50 individuals all who completed the study, ranged from 18 to 68 years of age, 9 males, 41 females, 37 Caucasian, 12 Hispanic and 1 Asian.

Equipment used included Parke-Davis Hypoallergenic Readi Bandages (Patch) or the equivalent, and 1 ml volumetric syringe without a needle.

Procedure: Subjects were requested to bathe or wash as usual before arrival at the facility. The inner forearm region, midway between the wrist and elbow, was designated as the test area. Two, 2 cm by 2 cm (4 cm2), test sites are delineated using a gentian violet surgical skin marker and standard template. The test material 0-5277 (Hest G-18-0) is evenly applied directly to the skin of the test site number 2 and 0.2 ml of the test material 0-5276 (10% benzoyl peroxide) was dispensed onto two occlusive, hypoallergenic patches. The patches were then affixed directly to the skin of the forearm test site number 1 and test site number 2. Subjects were dismissed with instructions not to wet or expose the test area to direct sunlight. After 24 hours the patch was removed at the facility and test sites were evaluated by trained laboratory personnel, recorded as 0 Hr. In the event of an adverse reaction, the area of erythema and edema was measured. The edema was estimated by the evaluation of the skin with respect to the contour of the unaffected normal skin. Reactions were scored again 24 hours following the initial evaluation, recorded as 24 Hr. Subjects were instructed to report any delayed reactions which might occur after the final reading.

The scoring scale used is described in Table 1.

TABLE 1

Scoring Scale and Definition of Symbols

| | |
|---|---|
| 0 | No evidence of any effect |
| ? | (Barely perceptible) minimal faint (light pink) uniform or spotty erythema |
| 1 | (Mild) pink uniform erythema covering most of contact site |
| 2 | (Moderate) pink\red erythema visibly uniform in entire contact area |
| 3 | (Marked) bright red erythema with accompanying edema, petechiae or papules |
| 4 | (Severe) deep red erythema with vesiculation or weeping with or without edema |
| Dc | Discontinued due to absence of subject on evaluation date |
| 5 | Skin stained from pigment in product |
| T | Tan |

NOTE:
All technical employees of AMA LABORATORIES, INC. are required to take and pass a visual discrimination examination conducted by a Board Certified Ophthalmologist using the Farnsworth-Munsell 100 Hue Test as published; which determines a person's ability to discern color against a black background. This test was additionally modified to include a flesh tone background more nearly approaching actual use conditions, wherein erythematous skin is graded according to intensity.

Results: Grade 1 irritation was observed in the majority of test panelists treated with the test material 0-5276 (10% benzoyl peroxide) and in four test panelist treated with test materials 0-5277 (Hest G-18-0) and 0-5276 (10% benzoyl peroxide). No other adverse reactions of any kind were noted during the course of this study. The complete date from the study is provided in Table 2 (Hest G-18-0 and 10% benzoyl peroxide) and Table 3 (10% benzoyl peroxide only)

TABLE 2

Summary of Results (occlusive patch) test materials 0-5276 and 0-5277 (Hest and 10% benzoyl peroxide)

| SUBJECT | | | | RESPONSE | |
|---|---|---|---|---|---|
| NO. | ID | RACE | SEX | 0 HR | 24 HR |
| 1 | 00 0016 | H | F | ? | ? |
| 2 | 05 3972 | C | F | 0 | ? |
| 3 | 11 4302 | C | F | 0 | 0 |
| 4 | 35 8496 | H | M | 0 | 0 |
| 5 | 36 1000 | C | M | ? | 0 |
| 6 | 40 1523 | C | F | ? | ? |
| 7 | 40 1589 | C | F | 0 | ? |
| 8 | 42 8272 | C | F | ? | ? |
| 9 | 44 6325 | C | F | 0 | 1 |
| 10 | 46 5197 | C | F | 0 | 0 |
| 11 | 48 1438 | C | F | 0 | ? |
| 12 | 48 2063 | C | F | 0 | 0 |
| 13 | 52 2026 | H | M | 0 | ? |
| 14 | 54 0345 | C | F | ? | ? |
| 15 | 54 5868 | C | F | ? | 0 |
| 16 | 54 9123 | H | F | 0 | 0 |
| 17 | 56 9543 | C | F | 0 | ? |
| 18 | 58 4622 | C | F | 0 | 0 |
| 19 | 58 4837 | C | F | 0 | ? |
| 20 | 58 7519 | C | F | 0 | 0 |
| 21 | 60 4541 | C | F | ? | ? |
| 22 | 60 5932 | C | F | ? | ? |
| 23 | 60 7847 | C | F | 0 | ? |
| 24 | 62 1181 | C | F | ? | ? |
| 25 | 62 4269 | C | F | ? | 0 |
| 26 | 62 5227 | H | F | ? | ? |
| 27 | 62 7588 | C | F | 0 | ? |
| 28 | 62 8070 | H | F | 0 | 0 |
| 29 | 64 4259 | C | M | 0 | ? |
| 30 | 66 1286 | C | F | ? | ? |
| 31 | 66 5617 | C | F | 1 | 1 |
| 32 | 66 8507 | C | M | 0 | ? |
| 33 | 66 9328 | H | M | 0 | 0 |
| 34 | 68 0458 | C | M | ? | 0 |
| 35 | 70 1220 | C | F | 0 | ? |
| 36 | 70 6695 | C | F | 0 | 0 |
| 37 | 70 7182 | A | F | ? | ? |
| 38 | 72 3637 | H | F | 0 | 1 |
| 39 | 72 7036 | C | F | ? | ? |
| 40 | 72 8719 | C | F | ? | ? |
| 41 | 74 4514 | C | F | 0 | ? |
| 42 | 74 5185 | C | F | ? | ? |
| 43 | 76 7056 | C | F | 0 | 0 |
| 44 | 82 7507 | H | F | 0 | ? |
| 45 | 86 1558 | C | M | 0 | ? |
| 46 | 86 8996 | C | F | 0 | 1 |
| 47 | 90 5388 | C | F | ? | 0 |
| 48 | 90 6566 | H | F | 0 | 0 |
| 49 | 92 7220 | C | M | 0 | ? |
| 50 | 94 2860 | H | F | ? | ? |

TABLE 3

Summary of Results (occlusive patch) test material 0-5276 (10% benzoyl peroxide) only

| SUBJECT | | | | RESPONSE | |
|---|---|---|---|---|---|
| NO. | ID | RACE | SEX | 0 HR | 24 HR |
| 1 | 00 0016 | H | F | ? | ? |
| 2 | 05 3972 | C | F | 1 | 1 |
| 3 | 11 4302 | C | F | 0 | ? |
| 4 | 35 8496 | H | M | ? | ? |
| 5 | 36 1000 | C | M | 1 | 1 |
| 6 | 40 1523 | C | F | ? | ? |
| 7 | 40 1589 | C | F | 1 | 1 |
| 8 | 42 8272 | C | F | ? | ? |
| 9 | 44 6325 | C | F | 1 | 1 |
| 10 | 46 5197 | C | F | ? | ? |

TABLE 3-continued

Summary of Results (occlusive patch) test material 0-5276 (10% benzoyl peroxide) only

| | SUBJECT | | | RESPONSE | |
|---|---|---|---|---|---|
| NO. | ID | RACE | SEX | 0 HR | 24 HR |
| 11 | 48 1438 | C | F | 1 | 1 |
| 12 | 48 2063 | C | F | ? | 0 |
| 13 | 52 2026 | H | M | 1 | 1 |
| 14 | 54 0345 | C | F | 1 | 1 |
| 15 | 54 5868 | C | F | 1 | 1 |
| 16 | 54 9123 | H | F | ? | ? |
| 17 | 56 9543 | C | F | 1 | 1 |
| 18 | 58 4622 | C | F | ? | 0 |
| 19 | 58 4837 | C | F | 1 | 1 |
| 20 | 58 7519 | C | F | 0 | ? |
| 21 | 60 4541 | C | F | 1 | 1 |
| 22 | 60 5932 | C | F | 1 | 1 |
| 23 | 60 7847 | C | F | 1 | 1 |
| 24 | 62 1181 | C | F | 1 | 1 |
| 25 | 62 4269 | C | F | 1 | 1 |
| 26 | 62 5227 | H | F | ? | ? |
| 27 | 62 7588 | H | F | 1 | 1 |
| 28 | 62 8070 | H | F | ? | ? |
| 29 | 64 4259 | C | M | 1 | 1 |
| 30 | 66 1286 | C | F | 1 | 1 |
| 31 | 66 5617 | C | F | 1 | 1 |
| 32 | 66 8507 | C | M | 1 | 1 |
| 33 | 66 9328 | H | M | 0 | ? |
| 34 | 68 0458 | C | M | 1 | 1 |
| 35 | 70 1220 | C | F | 1 | 1 |
| 36 | 70 6695 | C | F | 1 | 1 |
| 37 | 70 7182 | A | F | ? | ? |
| 38 | 72 3637 | H | F | 1 | 1 |
| 39 | 72 7036 | C | F | 1 | 1 |
| 40 | 72 8719 | C | F | 1 | 1 |
| 41 | 74 4514 | C | F | 1 | 1 |
| 42 | 74 5185 | C | F | ? | ? |
| 43 | 76 7056 | C | F | ? | 0 |
| 44 | 82 7507 | H | F | 1 | 1 |
| 45 | 86 1558 | C | M | 1 | 1 |
| 46 | 86 8996 | C | F | 1 | 1 |
| 47 | 90 5388 | C | F | 1 | 1 |
| 48 | 90 6566 | H | F | ? | ? |
| 49 | 92 7220 | C | M | 1 | 1 |
| 50 | 94 2860 | H | F | ? | ? |

Figure 3:
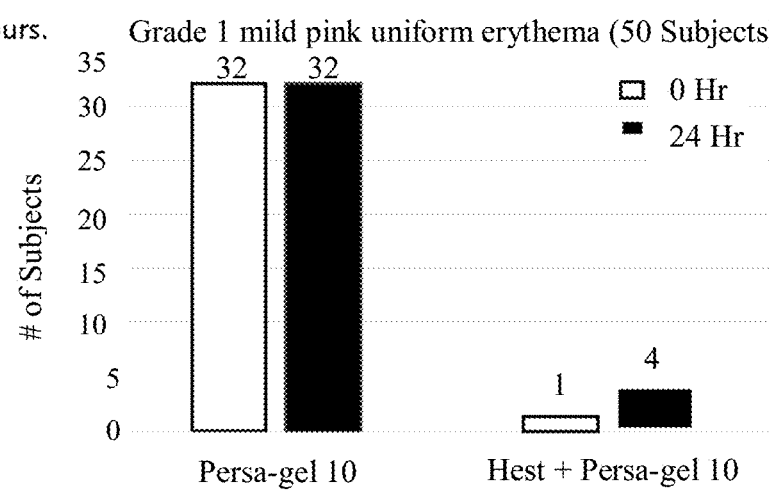
FIG. 3 depicts the results of a 24 hour occluded patch study comparing the application of persa-gel 10 (10% benzoyl peroxide) with the application of Hest G-18-0 prior to the application of the 10% benzoyl peroxide.

Conclusion: Hest G-18-0 (0-5277; Client No.: Cosmetic Emollient Gel RF1507-25 2-12-16) reduced skin irritation responses when applied topically prior to application of 10% benzoyl peroxide (0-5276; Client No.: Commercial acne product persa-gel 10) under 24 hour occlusive patch conditions as described herein and when compared to skin irritation responses observed on the test sites treated with the test material 10% benzoyl peroxide alone. FIG. 3 summarizes the results as a bar graph.

Example 4: Formulations

Hest Irritation Mitigation Emollient Gel for pre, post, or dual chamber application with 2.5% to 10% benzoyl peroxide topical OTC, see Table 4. As used in the test of Example 3.

TABLE 4

Emollient Thin Gel

| Phase | Trade Name | Supplier | INCI | % W/W |
|---|---|---|---|---|
| A | Hest G-18-0 | Global Seven | Glycereth-18 and Glycereth-18 Ethylhexanoate | 65.00 |
| B | Methocel™ 40-0100 PCG | Nexeo Solutions | Hydroxypropyl Methylcellulose | 3.00 |
| C | Deionized water | QB3 | Water | 31.94 |
| D | Trolamine 99 N.F | CoastSouthwest | Triethanolamine | 0.06 |

Slowly add B into A with vigorous mixing. Mix until all solids are dispersed using homogenizer at 4000 rpm speed. Add C and D individually and continue mix until ingredient is smooth & lump free, about 1 hour.

100.00

Benzoyl peroxide Cream Gel, see Table 5.

TABLE 5

Benzoyl peroxide Cream Gel

| Phase | Trade Name | Supplier | INCI | % W/W |
|---|---|---|---|---|
| A | Water | QB3 | Water | 83.30 |
| A | Glycerin | Jeen Int. | Glycerin | 8.00 |
| A | Sensidin DO | Ross/Schülke Inc | Octenidine HCl, Ethylhexylglycerin | 1.00 |

Add Water to the main batch. Begin homogenizer mixing at moderation speed (25,000 rpm), then add Phase A ingredients.

| B | Benzoyl peroxide (40% Solution) | Vantage Specialty Ingredients | Benzoyl peroxide | 2.50 |

TABLE 5-continued

Benzoyl peroxide Cream Gel

| Phase | Trade Name | Supplier | INCI | % W/W |
|---|---|---|---|---|
| B | DermalRX CKW | Biocogent | Curcuma Wenyujin/Curcuma KwangsiensisRhizome Extract | 0.20 |
| B | Simulgel 600 | Seppic | Acrylamide/Sodium Acryloyldimethyl Taurate Copolymer, Isohexadecane, Polysorbate 80 | 3.50 |
| B | Gransil DMSB | Grant Industries | Dimethicone, Polysilicone-11, Butyrospermum Parkii (Shea) Butter | 1.00 |
| | Add phase B Ingredients individually to A mixture, homogenizing at the same speed until smooth & lump free, then add C. |
| C | Sepimat HBV | Seppic | Methyl Methacrylate Crosspolymer | 0.50 |
| | Continue mixing until Sepimat HBV is evenly dispersed |
|  |  |  |  | 100.00 |

Benzoyl peroxide Cream Gel with Hest G-18-0 in a single composition, see Table 6.

TABLE 6

Benzoyl peroxide Cream Gel with Hest G-18-0

| Phase | Trade Name | Supplier | INCI | % W/W |
|---|---|---|---|---|
| A | Water | QB3 | Water | 53.30 |
| A | Emollient Thin Gel | RF1507-22 | Glycereth-18 and Glycereth-18 Ethylhexanoate, Water, Hydroxypropyl Methylcellulose, TEA | 40.00 |
| A | Sensidin DO | Ross/Schülke Inc | Octenidine HCl, Ethylhexylglycerin | 1.00 |
| | Add Water to the main batch. Begin homogenizer mixing at moderate speed (25,000 rpm). Then add Phase A ingredients. Mix until smooth & lump free. |
| B | Benzoyl peroxide (40% solution) | Vantage Specialty Ingredients | Benzoyl peroxide | 2.50 |
| B | DermalRX CKW | Biocogent | Curcuma Wenyujin/Curcuma KwangsiensisRhizome Extract | 0.20 |
| B | Simulgel 600 | Seppic | Acrylamide/Sodium Acryloyldimethyl Taurate Copolymer, Isohexadecane, Polysorbate 80 | 1.50 |
| B | Gransil DMSB | Grant Industries | Dimethicone, Polysilicone-11, Butyrospermum Parkii (Shea) Butter | 1.00 |
| | Add phase B Ingredients individually to A mixture, homogenizing at the same speed until smooth & lump free, then add C. |
| C | Sepimat HBV | Seppic | Methyl Methacrylate Crosspolymer | 0.50 |
| | Continue mixing until Sepimat HBV is evenly dispersed. |
|  |  |  |  | 100.00 |

Hest Irritation Mitigation Toner Serum for pre, post, or dual chamber application with 2.5% to 10% benzoyl peroxide topical OTC, see Table 7.

TABLE 7

Hest Toner Serum

| Phase | Trade Name | Supplier | INCI | % W/W |
|---|---|---|---|---|
| A | Hest G-18-0 | Global Seven | Glycereth-18 and Glycereth-18 Ethylhexanoate | 12.00 |
| A | Lipacide C8G | Seppic | Capryloyl Glycine | 1.50 |
| A | Tris Amino Ultra PC | Angus | Tromethamine | 0.50 |
| A | Botanistat PF 64 | Botanigenics | Phenoxyethanol, Caprylyl Glycol, Ethylhexylglycerin, Hexylene Glycol | 1.00 |
| A | Sensidin DO | Schülke Inc. | Propylene glycol (and) Ethylhexylglycerin (and) Octenidine HCl | 1.00 |
| A | Distinctive Blueberry 5P | Resources of Nature | Propanediol, VACCINIUM ANGUSTIFOLIUM (BLUEBERRY) FRUIT EXTRACT | 2.00 |

Disperse Phase A at Room Temperature. Start Heating the Phase to 50° C. while mixing. After everything is dissolved, lower the temp to 30-35° C. The batch should be clear.

| Phase | Trade Name | Supplier | INCI | % W/W |
|---|---|---|---|---|
| B | Water | QB3 Lab | Water | 64.00 |
| B | ESP Sugar Cane Alcohol 190, SDA 40B | Earth Supplied Products, LLC | Alcohol | 10.00 |

Add phase B ingredients to A with propeller mixing at 25-30° C.

| Phase | Trade Name | Supplier | INCI | % W/W |
|---|---|---|---|---|
| C | Glycerin | USP | Glycerin | 3.76 |
| C | Butylene Glycol | | Butylene Glycol | 4.00 |
| C | Polysurf 67CS | | Cetyl Hydroxyethylcellulose | 0.16 |
| C | Distinctive Hyaluronate 20 | Resources of Nature | Sodium Hyaluronate | 0.08 |

Pre-mix phase C under high shear propeller at 80° C. for one hour. Cool. Allow to swell for 24 hours. Add Phase C to A/B with propeller at RT conditions.

100.00

OTC Hest Irritation Mitigation Toner for pre, post, or dual chamber application with 2.5% to 10% benzoyl peroxide topical OTC, see Table 8.

TABLE 8

OTC Hest Toner

| Phase | Trade Name | Supplier | INCI | % W/W | % W/W | % W/W |
|---|---|---|---|---|---|---|
| A | Salicylic Acid | | Salicylic Acid | 0.50 | 0.50 | 0.50 |
| A | Hest G-18-0 | Global Seven | Glycereth-18 and Glycereth-18 Ethylhexanoate | 12.00 | 13.00 | 12.00 |
| A | Lipacide C8G | Seppic | Capryloyl Glycine | 1.00 | 0.70 | 0.00 |
| A | Tris Amino Ultra PC | Angus | Tromethamine | 0.50 | 0.50 | |
| A | Botanistat PF 64 | Botanigenics | Phenoxyethanol, Caprylyl Glycol, Ethylhexylglycerin, Hexylene Glycol | 1.00 | 1.00 | 1.00 |
| A | Sensidin DO | Schulke Inc. | Propylene glycol (and) Ethylhexylglycerin (and) Octenidine HCl | 1.00 | 1.00 | 1.00 |
| A | Distinctive Blueberry 5P | Resources of Nature | Propanediol, VACCINIUM ANGUSTIFOLIUM (BLUEBERRY) FRUIT EXTRACT | 2.00 | 1.50 | 1.50 |

TABLE 8-continued

OTC Hest Toner

| Phase | Trade Name | Supplier | INCI | % W/W | % W/W | % W/W |
|---|---|---|---|---|---|---|

Disperse Phase A at Room Temperature. Start Heating the Phase to 50° C. while mixing. After everything is dissolved, lower the temp to 30-35° C. The batch should be clear.

| Phase | Trade Name | Supplier | INCI | % W/W | % W/W | % W/W |
|---|---|---|---|---|---|---|
| B | Water | QB3 Lab | Water | 66.00 | 64.80 | 63.00 |
| B | Gransolve DMI | Grant Industries | Dimethyl Isosorbide | | 1.00 | |
| B | ESP Sugar Cane Alcohol 190, SDA 40B | Earth Supplied Products, LLC | Alcohol | 10.00 | 10.00 | 10.00 |
| B | RF Gel 12 RON16-73-2 | Resources of Nature | Butylene Glycol, Glycerin, Cetyl Hydroxyethylcellulose, Sodium Hyaluronate | 6.00 | 6.00 | 6.00 |

Mix Phase B until RF Gel is dissolved. Add Phase B slowly to Phase A at 30-35° C. Continue mixing until the batch is uniform and clear.

| | | | | 100.00 | 100.00 | 100.00 |
|---|---|---|---|---|---|---|
| | | | pH at RT | 4.15 | 4.29 | 4.40 |
| | | | pH after 24 hours at RT | 4.24 | | |

Hest Wipes for pre-application with 2.5% to 10% benzoyl peroxide topical OTC, see Table 9.

TABLE 9

Hest Wipes

| Phase | Trade Name | Supplier | INCI | % W/W |
|---|---|---|---|---|
| A | Hest G-18-0 | Global Seven | Glycereth-18 and Glycereth-18 Ethylhexanoate | 40.00 |
| B | ESP Sugar Cane Alcohol 190, SDA 40B | TCR/Earth Supplied Products, LLC | Alcohol | 35.00 |
| C | Water | QB3 | Water | 23.40 |

Add phase A ingredients to the main batch with mixing.

| | | | | |
|---|---|---|---|---|
| B | Dragosantol ® 100 | Symrise | Bisabolol | 0.10 |
| B | Sensidin DO | Ross/Schülke Inc. | Ethylhexylglycerin, Octenidine HCl | 1.00 |
| B | TEGO ® SML 20 | Glenn/Evonik | Polysorbate 20 | 0.50 |

Premix B. Then add to phase A with mixing

| | | | | 100.00 |
|---|---|---|---|---|

Hest Irritation Mitigation Gel for pre, post, or dual chamber application with 2.5% to 10% benzoyl peroxide topical OTC, see Table 10.

TABLE 10

Hest Gel

| Phase | Trade Name | Supplier | INCI | % W/W |
|---|---|---|---|---|
| A | Hest G-18-0 | Global Seven | Glycereth-18 and Glycereth-18 Ethylhexanoate | 64.00 |
| A | Deionized water | QB3 | Water | 35.30 |

Disperse A in B under propeller mixing

| | | | | |
|---|---|---|---|---|
| B | Carbopol 980 Polymer | Nexeo Solutions/Lubrizol | Carbomer | 0.50 |
| C | Desamine | Indepent Chemical | GLucamine | 0.20 |

Start the homogenizer at high speed to disperse Carbopol. Mix until B evenly dispersed and lump free, then add C. Mix until smooth or 20 minutes at moderate speed (2,000 rpm).

| | | | | 100.00 |
|---|---|---|---|---|

Hest Irritation Mitigation Anhydrous Gel for pre, post, or dual chamber application with 2.5% to 10% benzoyl peroxide topical OTC, see Table 11.

TABLE 11

Hest Anydrous Gel

| Phase | Trade Name | Supplier | INCI | % W/W |
|---|---|---|---|---|
| A | Hest G-18-0 | Global Seven | Glycereth-18 and Glycereth-18 Ethylhexanoate | 65.00 |
| B | Dow Corning ® EL-7040 Hydro Elastomer Blend | Nexeo Solutions/Dow Corning | Caprylyl Methicone, PEG-12 Dimethicone/PPG-20 Crosspolymer | 35.00 |

Slowly add A into B with vigorous mixing. Mix until all solids are dispersed.

| | | | | 100.00 |
|---|---|---|---|---|

Hest Irritation Mitigation Lotion for pre, post, or dual chamber application with 2.5% to 10% benzoyl peroxide topical OTC, see Table 12.

TABLE 12

Hest Lotion

| Phase | Trade Name | Supplier | INCI | % W/W |
|---|---|---|---|---|
| A | Hest G-18-0 | Global Seven | Glycereth-18 and Glycereth-18 Ethylhexanoate | 15.00 |
| A | Simulgel 600 | Seppic | Acrylamide/Sodium Acryloyldimethyl Taurate Copolymer, Isohexadecane, Polysorbate 80 | 33.50 |
| A | Water | QB3 | Water | 70.50 |

Add Water to the main batch. Begin homogenizer mixing at moderation speed (25,000 rpm). Then add Phase A ingredients.

| A1 | Sensidin DO | Ross/Schülke Inc. | Ethylhexylglycerin, Octenidine HCI | 1.00 |
| B | Botanester EHP | DDChemco/Botanigenics | Ethylhexyl Palmitate | 2.00 |
| B | Gransil DMSB | Grant Industries | Dimethicone, Polysilicone-11, Butyrospermum Parkii (Shea) Butter | 5.00 |
| B | Botanester GC | DDChemco/Botanigenics | Caprylic/Capric Triglyceride | 3.00 |

Add A1 to the Water phase. Homogenizer mixing at moderation speed (25,000 rpm) Then add Phase B. Continue mixing until smooth.

100.00

Hest spot treatment adhesive dots for pre-application with 1.0% to 10% benzoyl peroxide topical, see Table 13.

TABLE 13

Hest Adhesive Acne Dots

| Phase | Trade Name | Supplier | INCI | % W/W |
|---|---|---|---|---|
| A | Hest G-18-0 | Global Seven | Glycereth-18 and Glycereth-18 Ethylhexanoate | 37.50 |
| A | PVP K-90 | Ashland | PVP | 1.00 |
| A | ESP Sugar Cane Alcohol 190, SDA 40B | TCR/Earth Supplied Products, LLC | Alcohol | 35.00 |
| A | Water | QB3 | Water | 23.40 |

Add phase A ingredients to the main batch with mixing.

| B | Dragosantol ® 100 | Symrise | Bisabolol | 0.10 |
| B | Cabosil M-5 | Cabot | Silica | 0.50 |
| B | Sensidin DO | Ross/Schülke Inc. | Ethylhexylglycerin, Octenidine HCI | 1.00 |
| B | TEGO ® SML 20 | Glenn/Evonik | Polysorbate 20 | 0.50 |

Premix B. Then add to phase A with mixing 100.00

What is claimed is:

1. A topical composition comprising:
   a first composition containing about 5% by weight of benzoyl peroxide and a cosmetically acceptable excipient, and does not contain adapalene, and
   a second composition containing about 15% Hest G-18-0 and a cosmetically acceptable excipient,
   wherein the first composition and the second composition are combined before use to form the topical composition and wherein the benzoyl peroxide is solubilized in the Hest G-18-0.

2. The topical composition of claim 1, wherein the cosmetically acceptable excipient of the first composition is selected from the group consisting of polysaccharide polymer, glycerin, butylene glycol, acrylamide/sodium acryloyodimethyltaurate copolymer, isohexadecane, phenoxyethanol, polysorbate 80, ethylhexylglycerin, sodium hydroxide, dipropylene glycol, pentylene glycol, polyethylene glycol, ethanol, water, and combinations thereof.

3. The topical composition of claim 1, wherein the first composition further comprises an effective amount of tocopherol.

4. The topical composition of claim 1, wherein the cosmetically acceptable excipient of the second composition is selected from the group consisting of polysaccharide polymer, glycerin, butylene glycol, propanediol, dimethyl isosorbide, acrylamide/sodium acryloyodimethyltaurate copolymer, propylene glycol, phenoxyethanol, isohexadecane, methyl methacrylate crosspolymer, polysorbate 80, ethylhexylglycerin, 1,2-hexanediol, cetyl hydroxyethylcellulose, dipropylene glycol, pentylene glycol, polyethylene glycol, ethanol, water, and combinations thereof.

5. The topical composition of claim 1, wherein the second composition further comprises an effective amount of *Vaccinium angustifolium* (Blueberry) fruit extract.

6. The topical composition of claim 1, wherein the benzoyl peroxide is at a concentration of about 2.5% by weight of the topical composition upon combination of the first composition and the second composition.

7. The topical composition of claim 1, wherein the Hest G-18-0 is at a concentration of about 7.5% by weight of a topical composition upon combination of the first composition and the second composition.

8. A method of treating acne comprising applying to a subject's skin a topical composition comprising:
   a first composition containing about 5% by weight of benzoyl peroxide and a cosmetically acceptable excipient, and does not contain adapalene, and
   a second composition containing about 15% Hest G-18-0 and a cosmetically acceptable excipient,
   wherein the first composition and the second composition are combined before use to form the topical composition and wherein the benzoyl peroxide is solubilized in the Hest G-18-0.

9. The method of claim 8, wherein the composition reduces skin erythema, skin irritation, drying of the skin, cracking of the skin, and appearance of white residue on the skin.

10. The method of claim 8, wherein subject compliance is increased.

11. The method of claim 8, wherein the benzoyl peroxide efficacy is increased as part of the topical composition.

12. The method of claim 8, wherein the cosmetically acceptable excipient of the first composition is selected from the group consisting of polysaccharide polymer, glycerin, butylene glycol, acrylamide/sodium acryloyodimethyltaurate copolymer, isohexadecane, phenoxyethanol, polysorbate 80, ethylhexylglycerin, sodium hydroxide, dipropylene glycol, pentylene glycol, polyethylene glycol, ethanol, water, and combinations thereof.

13. The method of claim 8, wherein the first composition further comprises an effective amount of tocopherol.

14. The topical composition of claim 8, wherein the cosmetically acceptable excipient of the second composition is selected from the group consisting of polysaccharide polymer, glycerin, butylene glycol, propanediol, dimethyl isosorbide, acrylamide/sodium acryloyodimethyltaurate copolymer, propylene glycol, phenoxyethanol, isohexadecane, methyl methacrylate crosspolymer, polysorbate 80, ethylhexylglycerin, 1,2-hexanediol, cetyl hydroxyethylcellulose, dipropylene glycol, pentylene glycol, polyethylene glycol, ethanol, water, and combinations thereof.

15. The method of claim 8, wherein the second composition further comprises an effective amount of *Vaccinium angustifolium* (Blueberry) fruit extract.

16. The method of claim 8, wherein the benzoyl peroxide is at a concentration of about 2.5% by weight of the topical composition upon combination of the first composition and the second composition.

17. The method of claim 8, wherein the Hest G-18-0 is at a concentration of about 7.5% by weight of a topical composition upon combination of the first composition and the second composition.

18. A dual chamber package comprising:
a first chamber containing a first composition containing about 5% by weight of benzoyl peroxide and a cosmetically acceptable excipient, and does not contain adapalene; and
a second chamber containing a second composition containing about 15% by weight of Hest G-18-0 and a cosmetically acceptable excipient,
wherein the first composition and the second composition are combined before application to a subject's skin to form a topical composition and wherein the benzoyl peroxide is solubilized in the Hest G-18-0.

19. The package of claim 18, wherein the topical composition is applied to the skin of a subject and reduces skin erythema, skin irritation, drying of the skin, cracking of the skin, and appearance of white residue on the skin.

20. The package of claim 19, wherein the subject's use and compliance of the topical composition is increased.

21. The package of claim 18, wherein the benzoyl peroxide efficacy is increased as part of the topical composition.

22. The package of claim 18, wherein the cosmetically acceptable excipient of the first composition is selected from the group consisting of polysaccharide polymer, glycerin, butylene glycol, acrylamide/sodium acryloyodimethyltaurate copolymer, isohexadecane, phenoxyethanol, polysorbate 80, ethylhexylglycerin, sodium hydroxide, dipropylene glycol, pentylene glycol, polyethylene glycol, ethanol, water, and combinations thereof.

23. The package of claim 18, wherein the first composition further comprises an effective amount of tocopherol.

24. The package of claim 18, wherein the cosmetically acceptable excipient of the second composition is selected from the group consisting of polysaccharide polymer, glycerin, butylene glycol, propanediol, dimethyl isosorbide, acrylamide/sodium acryloyodimethyltaurate copolymer, propylene glycol, phenoxyethanol, isohexadecane, methyl methacrylate crosspolymer, polysorbate 80, ethylhexylglycerin, 1,2-hexanediol, cetyl hydroxyethylcellulose, dipropylene glycol, pentylene glycol, polyethylene glycol, ethanol, water, and combinations thereof.

25. The package of claim 18, wherein the second composition further comprises an effective amount of *Vaccinium angustifolium* (Blueberry) fruit extract.

26. The package of claim 18, wherein the benzoyl peroxide is at a concentration of about 2.5% by weight of the topical composition upon combination of the first composition and the second composition.

27. The package of claim 18, wherein the Hest G-18-0 is at a concentration of about 7.5% by weight of a topical composition upon combination of the first composition and the second composition.

* * * * *